United States Patent
Stankowski (10) Patent No.: US 11,441,713 B2
(45) Date of Patent: Sep. 13, 2022

(54) CONNECTION CLAMPING DEVICE

(71) Applicant: Global Life Sciences Solutions USA LLC, Marlborough, MA (US)

(72) Inventor: Ralph Stankowski, Westborough, MA (US)

(73) Assignee: Global Life Sciences Solutions USA LLC, Marlborough, MA (US)

(*) Notice: Subject to any disclaimer, the term of this patent is extended or adjusted under 35 U.S.C. 154(b) by 268 days.

(21) Appl. No.: 15/759,973

(22) PCT Filed: Oct. 3, 2016

(86) PCT No.: PCT/EP2016/073545
§ 371 (c)(1),
(2) Date: Mar. 14, 2018

(87) PCT Pub. No.: WO2017/060188
PCT Pub. Date: Apr. 13, 2017

(65) Prior Publication Data
US 2018/0266600 A1    Sep. 20, 2018

Related U.S. Application Data

(60) Provisional application No. 62/237,939, filed on Oct. 6, 2015.

(51) Int. Cl.
| *F16L 33/23* | (2006.01) |
| *A61M 39/12* | (2006.01) |
| *F16L 33/22* | (2006.01) |
| *A61M 39/10* | (2006.01) |

(52) U.S. Cl.
CPC ............. *F16L 33/23* (2013.01); *A61M 39/12* (2013.01); *F16L 33/225* (2013.01); *A61M 2039/1066* (2013.01); *F16L 2201/10* (2013.01); *F16L 2201/44* (2013.01)

(58) Field of Classification Search
CPC ....... F16L 33/23; F16L 2201/10; A61M 39/12
USPC .................................................. 285/242, 241
See application file for complete search history.

(56) References Cited

U.S. PATENT DOCUMENTS

| 3,185,500 A | 5/1965 | Luther |
| 3,526,416 A | 9/1970 | Kish |
| 4,451,070 A | 5/1984 | Sauer |
| 4,723,948 A | 2/1988 | Clark et al. |

(Continued)

FOREIGN PATENT DOCUMENTS

| DE | 3520953 C1 | 9/1986 | |
| GB | 968973 A | * 9/1964 | .............. F16L 33/23 |

(Continued)

OTHER PUBLICATIONS

PCT International Search Report for PCT Application No. PCT/EP2016/073545 dated Jan. 9, 2017 (8 pages).

(Continued)

*Primary Examiner* — David Bochna
(74) *Attorney, Agent, or Firm* — Eversheds Sutherland (US) LLP (57) ABSTRACT

A connection clamping device comprising two halves which are arranged to be connected and locked to each other by a locking mechanism around the a flexible tube, such that the flexible tube is compressed by a rib provided on the inner circumference of the connection clamping device.

7 Claims, 8 Drawing Sheets

(56) References Cited

U.S. PATENT DOCUMENTS

| | | | |
|---|---|---|---|
| 4,912,602 A | 3/1990 | Zurek et al. | |
| 5,074,600 A | 12/1991 | Weinhold | |
| 5,137,309 A | 8/1992 | Beagle | |
| 6,155,610 A * | 12/2000 | Godeau | F16L 33/02 285/242 |
| 7,370,889 B2 * | 5/2008 | Maunder | F16L 33/225 285/242 |
| 8,696,647 B2 * | 4/2014 | Bizup | A61M 39/12 604/535 |
| 8,888,140 B2 | 11/2014 | Stroempl et al. | |
| 10,352,488 B2 | 7/2019 | Barrientos | |
| 2006/0106365 A1 | 5/2006 | Lane et al. | |
| 2008/0221469 A1 * | 9/2008 | Shevchuk | F16L 33/23 600/532 |
| 2008/0319421 A1 | 12/2008 | Bizup et al. | |
| 2011/0163533 A1 | 7/2011 | Snyder et al. | |
| 2013/0060268 A1 | 3/2013 | Herrig | |
| 2013/0257041 A1 | 10/2013 | Peirce | |
| 2015/0167874 A1 | 6/2015 | Buerli et al. | |
| 2015/0308598 A1 | 10/2015 | Lewis et al. | |
| 2016/0146386 A1 | 5/2016 | Blake et al. | |

FOREIGN PATENT DOCUMENTS

| | | |
|---|---|---|
| JP | 2006097841 A | 4/2006 |
| WO | 2006/135227 A1 | 12/2006 |
| WO | 2015/191991 A1 | 12/2015 |
| WO | 2017/060188 A1 | 4/2017 |

OTHER PUBLICATIONS

PCT International Search Report for PCT Application No. PCT/EP2018/058605 dated Jul. 9, 2018 (4 pages).

Chinese Office Action for CN Application No. 201680058469.8 dated Feb. 19, 2020 (15 pages with English translation).

European Notice of Opposition for EP Application No. 16781316.1 dated Sep. 7, 2021 (47 pages).

* cited by examiner

CONNECTION CLAMPING DEVICE

CROSS REFERENCE TO RELATED APPLICATIONS

This application claims the priority benefit of PCT/EP2016/073545 filed on Oct. 3, 2016 which claims priority benefit of U.S. Provisional Application No. 62/237,939 filed Oct. 6, 2015. The entire contents of which are hereby incorporated by reference herein.

TECHNICAL FIELD OF THE INVENTION

The present invention relates to a connection clamping device and to a method for connecting flexible tubes to connection means.

BACKGROUND OF THE INVENTION

Flexible tubing/tubes are used for transferring fluids or gases in many different environments for example in bioprocessing, medical and food industry. The flexible tubing need to be connected to different components such as for example bags, sensors, fittings, ports or connectors of different types. Especially in for example the medical field and the bioprocessing field it is really important that these connections are leak proof and that no liquid will get trapped in the connection causing for example growth of bacteria.

A connection means of the connector, port or fitting to which the flexible tube typically is connected comprises often a barb. A commonly used way to perform the connection is to simply use a cable tie around the flexible tube and the connection means which has been provided protruding into the flexible tube. The cable tie is then suitably positioned below the barb. There are some drawbacks related to the use of cable ties in this context. One problem is that the compression of the flexible tube will not be evenly distributed over the whole circumference because of the head of the cable tie. Under the head of the cable tie the flexible tube will "bubble up" and this could cause leakage. If mold insert lines from the molding process also are present at the same location as the cable tie head the leakage problem could be even exaggerated. Another problem is that the strap of the cable tie which is left pointing out from the head after tightening is somewhat sharp and could possibly damage sensitive materials provided in vicinity. Often one needs to wrap the cable ties in bubble wrap to avoid damage. Still a further problem with the use of cable ties is that it is rather time consuming. The positioning and tightening of one cable tie can take around 1-2 minutes and in a typical bioprocessing environment there could be hundreds of such connections to be done.

A connection clamping device is described in for example U.S. Pat. No. 7,090,257. This connection clamping device comprises two parts which need to be threaded onto the flexible tube and then a tool is needed to fit these two parts over each other in order to compress the flexible tube over the connection means. One problem with this device is that these parts need to be slid over the flexible tube which can be tricky, especially since one of them fits close to the tube, i.e. the inner diameter of one of the parts is almost the same as the tube outer diameter. Furthermore the use of a tool is both tricky, it needs some force and precision, and time consuming.

SUMMARY

An object of the invention is to provide an improved connection clamping device for connecting flexible tubes to connection means.

A further object of the invention is to provide a connection clamping device that is easy to connect and reliable, i.e. leak proof and steady.

This is achieved in a connection clamping device arranged for connecting a flexible tube to a barbed end of a connection means, whereby the barbed end comprises a barb and the connection means during connection is arranged to protrude into an end of the flexible tube. According to the invention said connection clamping device comprises two halves which, during connection when the connection means protrudes into an end of the flexible tube, are arranged to be connected and locked to each other by a locking mechanism around the connection means and the flexible tube, such that the flexible tube is compressed against the connection means by a rib provided on the inner circumference of the connection clamping device.

Hereby a connection clamping device for connecting tubes to connection means is achieved that is fast and easily mounted with high precision and which seals the connection evenly over the whole circumference.

This is also achieved in a method for connecting a flexible tube to a connection means, said method comprising the steps of:
 providing the connection means protruding into an end of the flexible tube;
 providing a connection clamping device around the flexible tube and the connection means when the connection means protrudes into the tube, said connection clamping device comprises two halves which are connected and locked to each other during this step;
 squeezing the flexible tube against the connection means by a rib provided on a part of the inner surface of the connection clamping device around the circumference.

Hereby a method is achieved by which flexible tubes can be fast and easily connected to connection means with high precision and whereby a reliable connection is achieved.

Embodiments of the invention are described in the dependent claims.

DETAILED DESCRIPTION OF EMBODIMENTS

Figure 1A:
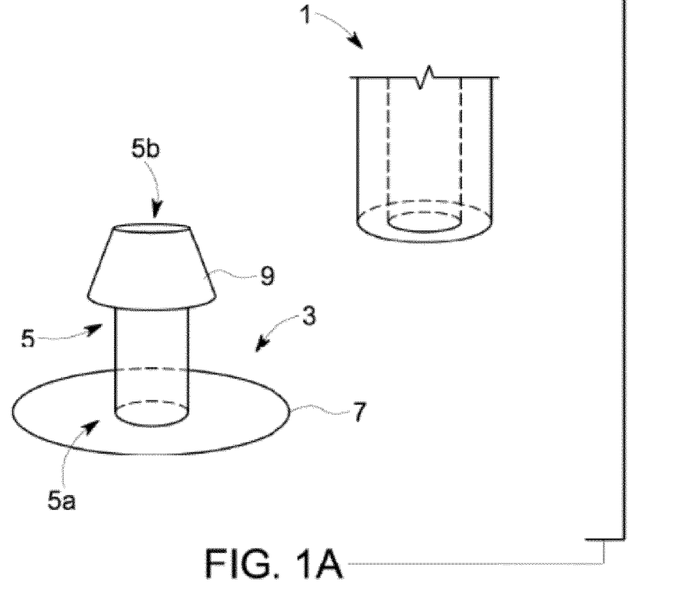
FIG. 1a shows schematically a flexible tube and a port.

FIG. 1a shows schematically a flexible tube 1 and a port 3. This kind of port 3 could be provided onto for example bags that need to be connected to other components such as flexible tubes. When connecting the flexible tube 1 to the port 3 the tube is simply slid over a connection means 5 of the port 3. The connection means 5 of the port 3 has the form of a short tube and is connected to a sealing part 7 of the port 3 in a first end 5a of the connection means 5. The sealing part 7 of the port 3 is in this embodiment shown to extend around the first end 5a of the connection means 5 in a perpendicular direction to the tube extension. The sealing part is adapted to be sealed to the device that should be connected to the flexible tube 1, such as for example a bag. A second end 5b of the connection means 5, which is positioned on the other end of the connection means 5 compared to the first end 5a, comprises usually a barb 9. This end is also called a barbed end 5b of the connection means 5. An outside diameter of the connection means 5 is typically close to but slightly bigger than an inner diameter of the flexible tube. A flexible tube to be connected to a connection means needs typically to be stretched to be slid over the barb and the connection means. Hereby no gap is provided between the connection means and the flexible tube.

Figure 1B:
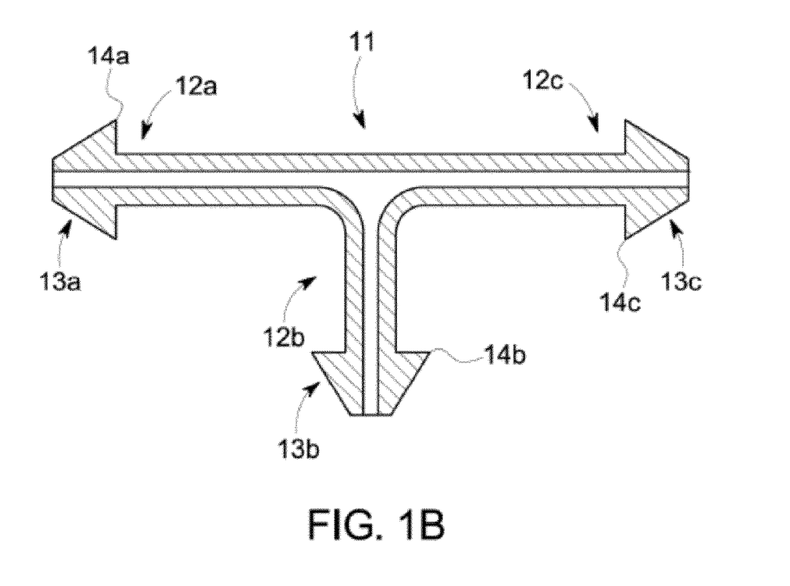
FIG. 1b shows schematically a connector.

FIG. 1b shows schematically a connector 11. This is a so called T connector. Such a connector can couple for example sensors, connectors, fittings and pumps. Other types of connectors such as Y connectors can also be used in this invention. The T connector comprises three connection means 12a, 12b, 12c pointing in different directions and being internally connected to each other. Each of the connection means 12a, 12b, 12c comprises a barbed end 13a, 13b, 13c, i.e. a barb 14a, 14b, 14c is provided towards the end of each of the connection means 12a, 12b, 12c. Flexible tubes are provided over the barbed ends during connection. This is further shown in FIG. 7.

Figure 2A:
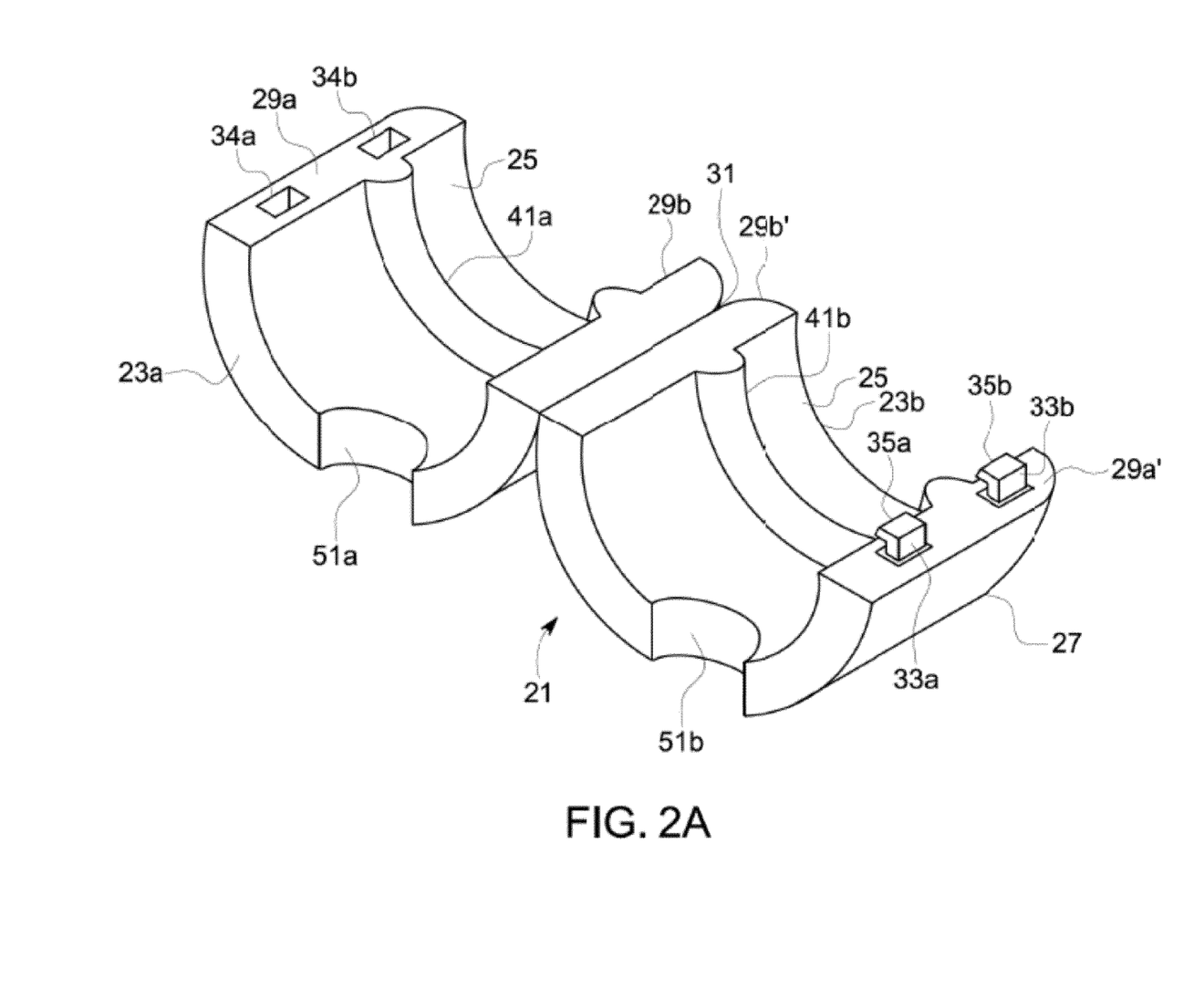
FIG. 2a shows schematically a connection clamping device according to one embodiment of the invention in an open position.

FIG. 2a shows schematically a connection clamping device 21 according to one embodiment of the invention in an open position. The connection clamping device 21 comprises a first half 23a and a second half 23b. The two halves 23a, 23b are each in the form of a half tube, i.e. when the two halves 23a and 23b are connected to each other a tube formed device is provided. Each half 23a, 23b of the connection clamping device 21 has an inner surface 25 and an outer surface 27 where inner and outer refer to inner and outer surface when the two halves are connected and a tubed formed device is provided. Each half 23a, 23b also has a first connection surface 29a, 29a' and a second connection surface 29b, 29b'. These connection surfaces 29a, 29a', 29b, 29b' of the two halves 23a, 23b are the surfaces contacting each other when the two halves are connected and form a tube formed part. In this embodiment the two halves 23a, 23b are connected to each other via a hinge 31 that can be a living hinge provided between the second connection surfaces 29b, 29b' of the two halves. Hereby the device is provided as one single part. The first connection surfaces 29a, 29a' comprise a snap locking mechanism. In this embodiment there is shown two protruding latches 33a, 33b on the first connection surface 29a' of the second half 23b and two corresponding recesses 34a, 34b on the first connection surface 29a of the first half 23a. The protruding latches 33a, 33b comprises each a barb 35a, 35b and correspondingly the recesses 34a, 34b are designed such that a snapping locking is achieved when the protruding latches 33a, 33b with their barbs 35a, 35b are provided into the recesses 34a, 34b. The number of latches and recesses can be varied. The design of the locking mechanism can be varied such as for example the use of a hook.

According to the invention a first part 41a of a first rib is provided along the inner surface 25 of the first half 23a and a second part 41b of a first rib is provided along the inner surface 25 of the second half 23b. The first and second parts of the first rib 41a, 41b are provided in a circumferential direction and will connect to the rib of the other half when the two halves 23a, 23b are connected such that a first rib is provided around the whole circumference of the inner surface of the tube formed part. The first and second parts of the first rib 41a, 41b are here shown to be in the form of a semi-circle revolved along the circumference of the inner surface 25. However the rib could also be in another form such as rectangular or with a triangular cross section. The function of the first rib 41a, 41b is that it should protrude into the flexible tube when connecting the tube to the port. The rib should be provided in such a position on the connection clamping device such that the rib is provided below a barb of the connection means to be connected to the flexible tube.

According to one embodiment of the invention the inner diameter of the connection clamping device 21 when the two halves 23a, 23b are connected is slightly larger than the outer diameter of the flexible tube (except from the location of the first rib). Hereby the only part of the connection clamping device 21 that is touching the flexible tube is the first rib 41a, 41b. The first rib 41a, 41b will compress the flexible tube and thereby compress the tube to the connection means as is the purpose of the invention. Because of the small empty space between the rest of the connection clamping device inner diameter and the outside diameter of the flexible tube any bubbling up of the tube as a consequence of the rib compressing and displacing the tube can be housed in this empty space without any additional forces on the locking mechanism. Hereby also the installation is easier and requires less force.

In one embodiment of the invention there is an indicator window 51a, 51b provided either in one of the two halves 23a, 23b or as shown in FIG. 2a in both the first and the second half 23a, 23b. The indicator window 51a, 51b is a recess in the wall of the halves on that side of the halves that will be provided opposite to the barbed end of the connection means during connection. When the connection clamping device 21 has been positioned over the flexible tube and the connection means for connecting them together the end of the tube should be seen through the indicator window 51, 51b. This ensures that the tube has been positioned correctly over the connection means. During use it can also always be checked that the tube still is in place by looking through the indicator window. For example, if the tube has been pulled by mistake it can easily be checked that the tube is still in a correct position over the connection means by only check that the tube can be seen through the indicator window 51a, 51b.

Figure 2B:
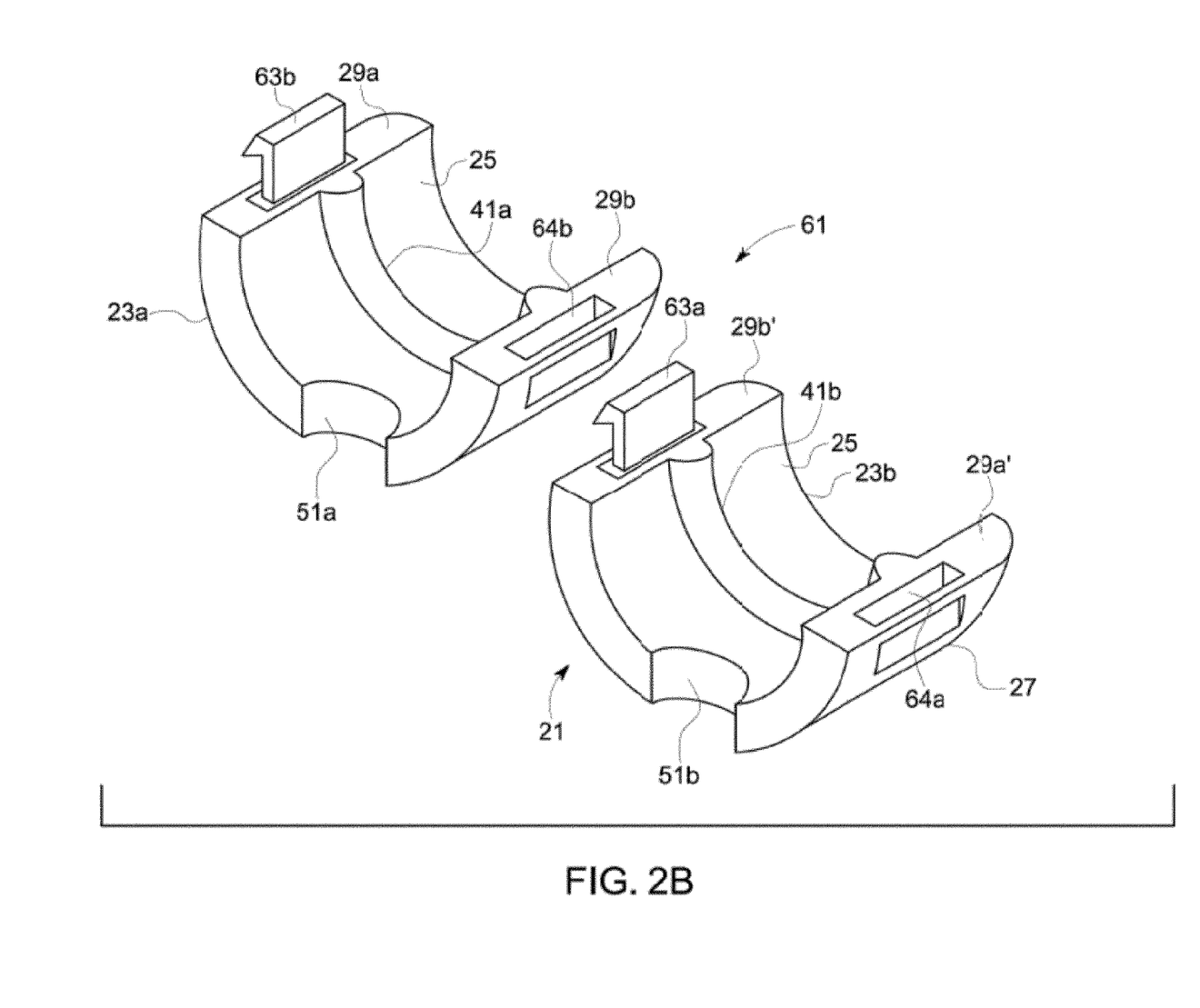
FIG. 2b shows schematically a connection clamping device according to another embodiment of the invention in an open position.

FIG. 2b shows schematically a connection clamping device 61 according to another embodiment of the invention in an open position. The difference from the connection clamping device 21 shown in FIG. 2a is only that there is no hinge connecting the two halves 23a, 23b. Most of the reference numbers are the same as in FIG. 2a and the description will not be repeated. Instead of a hinge connecting the two second connection surfaces 29b, 29b' a snap locking mechanism corresponding to the snap locking mechanism on the first connection surfaces 29a, 29a' is provided also to the second connection surfaces 29b, 29b'. In this embodiment one protruding latch 63a is provided on the second connection surface 29b' of the second half 23b and one protruding latch 63b is provided on the first connection surface 29a of the first half 23a and correspondingly one recess 64a is provided in the first connection surface 29a' of the second half 23b and one recess 64b is provided in the second connection surface 29b of the first half 23a. As discussed above the number of latches and recesses can be chosen.

Figure 3:
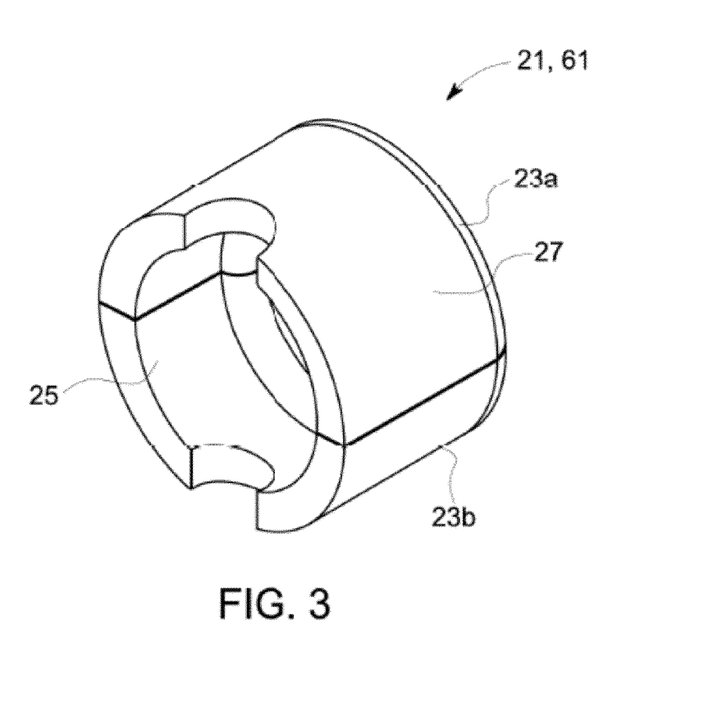
FIG. 3 shows the connection clamping device of FIG. 2a or 2b in a closed position.

FIG. 3 shows the connection clamping device of FIG. 2a or 2b in a closed position. Hereby the latches 33a, 33b, 63a, 63b have been provided into the recesses 34a, 34b, 64a, 64b and provide a snap locking mechanism. A short tube is formed with an outer surface 27 and an inner surface 25.

Figure 4:
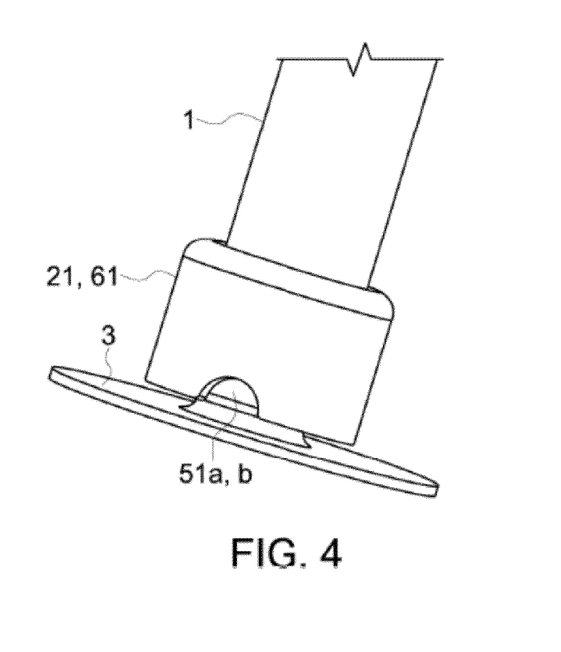
FIG. 4 shows the connection clamping device of FIG. 2a or 2b in closed position over the flexible tube and connection means hereby connecting the flexible tube to the connection means.

FIG. 4 shows the connection clamping device 21, 61 of FIG. 2a or 2b in closed position over a flexible tube 1 and a connection means 5 of a port 3 hereby connecting the flexible tube to the port. Here it can be seen through the indicator window 51a or 51b that the flexible tube 1 is in correct position. It can also be seen that the outer surface of the connection clamping device 21, 61 is smooth and will not damage any other components in the vicinity.

Figure 5A:
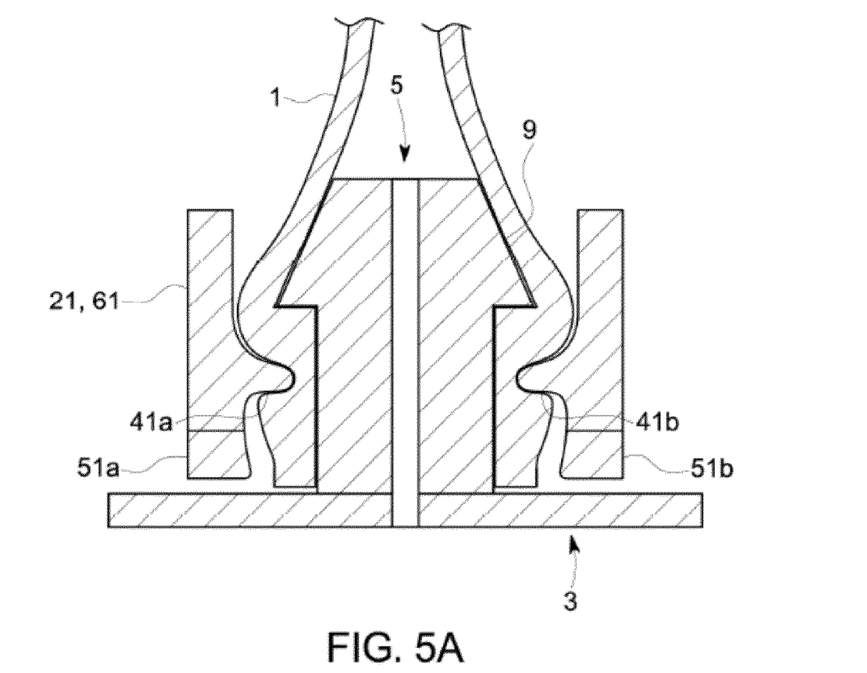
FIG. 5a shows schematically FIG. 4 in cross section.

FIG. 5a shows FIG. 4 in cross section. Here a connection means 5 of a port 3 as defined in relation to FIG. 1 can be seen. The connection means has also a barb 9. A flexible tube 1 is shown connected to the port 3 and a connection clamping device 21, 61 as described in relation to the FIGS. 2-4 is shown in connection position. The rib 41a, 41b is shown to compress the tube against the connection means 5 of the port 3 below the barb 9. The indicator windows 51a, 51b are also shown.

Figure 5B:
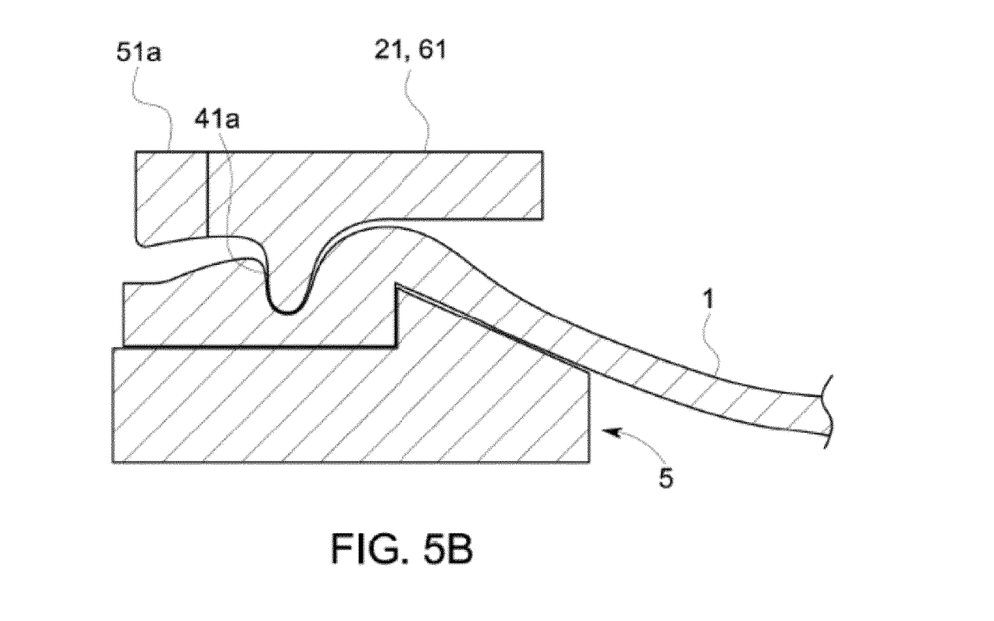
FIG. 5b shows schematically an enlarged view of the compression of the tube.

FIG. 5b shows schematically an enlarged view of the compression of the tube. Tube displacement can be seen. It can also be seen that the gap provided between the connection clamping device and the tube in all places except from where the rib is provided can house the tube displacement—or tube bubble up caused by the compressing of the tube from the rib.

Figure 6A:
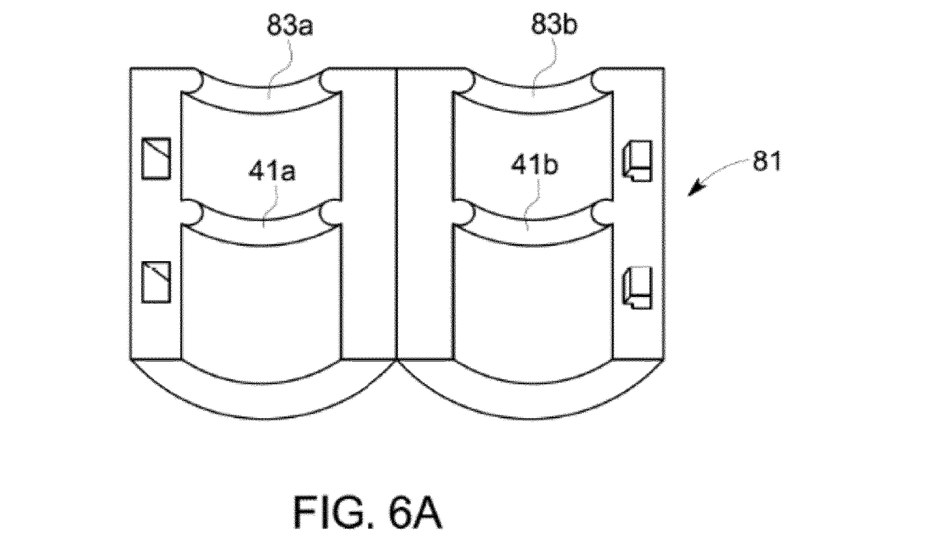
FIG. 6a shows schematically a connection clamping device according to another embodiment of the invention in an open position.

FIG. 6a shows schematically a connection clamping device 81 according to another embodiment of the invention in an open position. Almost all the details are exactly the same as in the embodiment shown in FIG. 2a so the reference numbers will be the same and the description will not be repeated. The difference is that in this embodiment a second rib 83a, 83b is provided in addition to the first rib 41a, 41b. This second rib 83a, 83b is provided in the end of the first and second halves 23a, 23b and is arranged to squeeze the tube against the connection means 5 just above the barb 9. This can be seen in FIG. 6b.

Figure 6B:
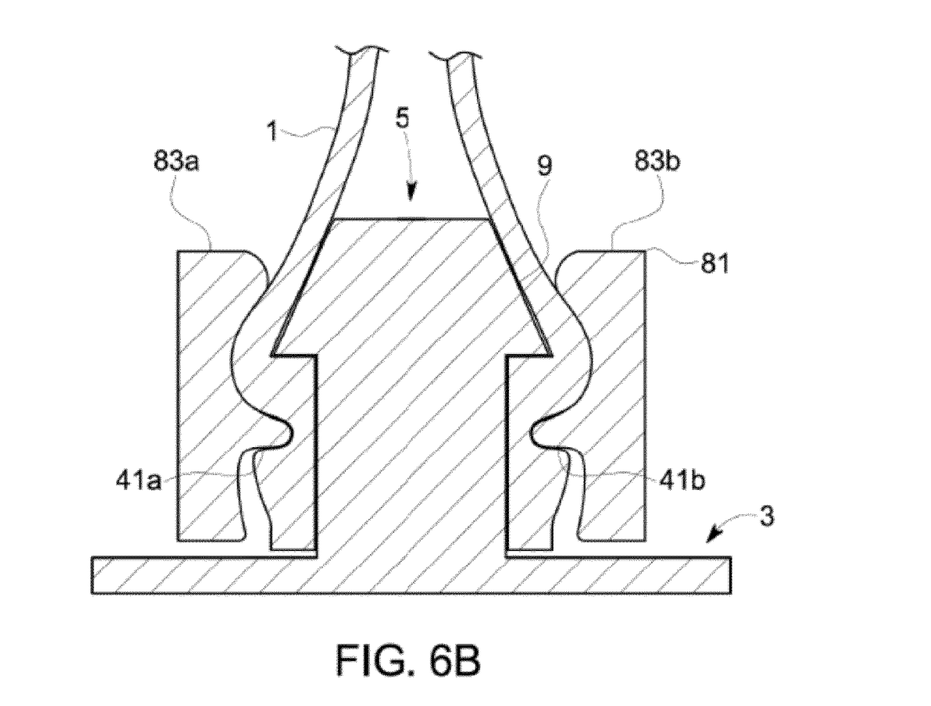
FIG. 6b shows schematically the connection clamping device of the embodiment of FIG. 6a in connected position and in cross section.

FIG. 6b shows schematically the connection clamping device 81 of the embodiment of FIG. 6a in connected position and in cross section. The first rib 41a, 41b is shown to squeeze the flexible tube 1 against the connection means 5 of the port 3 below the barb 9 and the second rib 83a, 83b is shown to squeeze the flexible tube 1 against the connection means 5 of the port 3 above the barb 9. An advantage with this embodiment is that it can take higher pressure.

Furthermore this embodiment seals in a location (the cone area) that doesn't need to have mold insert lines. This makes the seal more reliable. Suitably, this embodiment can include a feature that aligns the connection clamping device with the connection means in the axial direction. This feature is further shown and described in relation to FIG. 9. This feature will ensure that the second rib will seal against the coned surface of the barb.

Different sizes of the connection clamping device can be provided for different tube and connection means sizes. Different sizes could suitably be colored differently.

Figure 7:
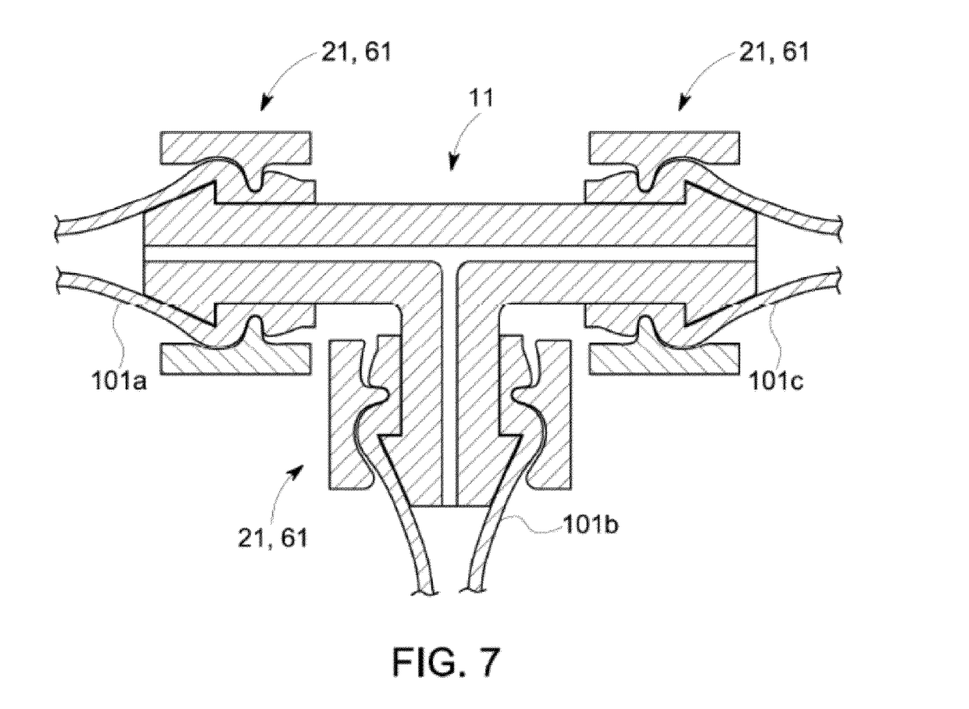
FIG. 7 shows schematically in cross section three flexible tubes connected by the use of three connection clamping devices according to the invention to a T connector.

FIG. 7 shows schematically in cross section three flexible tubes 101a, 101b, 101c connected to a T connector 11 (as shown in FIG. 1b) by the use of three connection clamping devices 21, 61 according to the invention.

Figure 8:
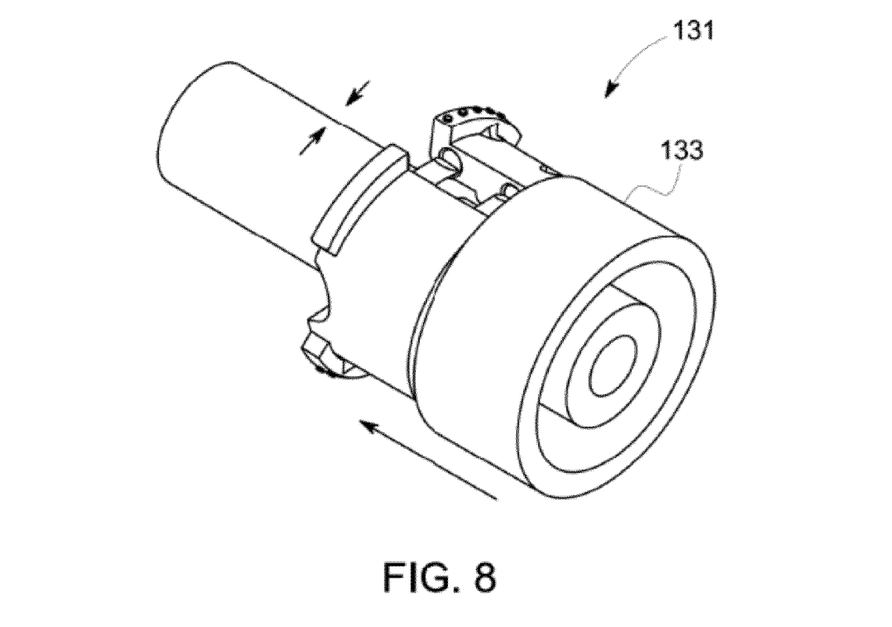
FIG. 8 shows schematically another embodiment of a connection clamping device according to the invention.

FIG. 8 shows schematically another embodiment of a connection clamping device 131 according to the invention. A different type of locking mechanism is provided instead of the latches and recesses described in relation to FIGS. 2a and 2b. In this embodiment the locking mechanism is a resilient sleeve 133 to be slid over the two halves when connected over the tube and connection means. In this Figure it is shown to be two separate halves but they could also be hinged to each other. The outer surface of the two halves could be provided with a means, such as a recess or a pattern for receiving such a sleeve.

Figure 9:
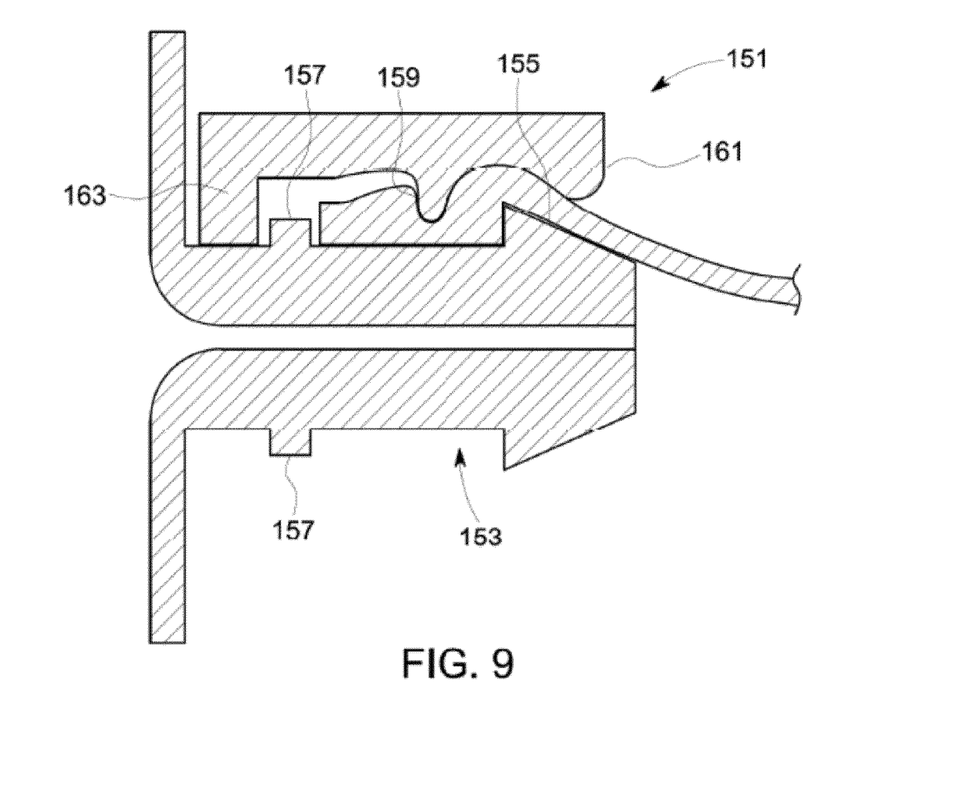
FIG. 9 shows schematically in cross section another embodiment of a connection clamping device according to the invention.

FIG. 9 shows schematically in cross section another embodiment of a connection clamping device 151 according to the invention. In this embodiment also the connection means 153 needs to be adapted. The connection means 153 is provided as usual with a barb 155 in one end but according to this embodiment there is also provided a connection means rib 157 in the other end. This connection means rib 157 is provided for keeping the connection clamping device 151 in correct position and for providing a first and a second rib 159, 161 (even more ribs could be provided) in correct sealing positions. For this purpose a positioning rib 163 is provided outermost in one of the ends of the connection clamping device 151. This is the end which will be provided opposite to the barbed end of the connection means when the connecting clamping means is connected. The positioning rib 163 and the connection means rib 157 will when the connection clamping device is provided be adjacent each other and assure the position of the connection clamping device. The positioning rib 163 does not need to be a rib over the whole circumference. It can instead be for example two or more rib parts provided one in each half of the connection clamping device. An advantage with this embodiment is that the second rib of the connection clamping device can be assured to be provided sealing against the cone part of the barb. It could be suitably to seal against the cone part of the barb because this part may not comprise any mold insert lines.

Further according to the invention a method for connecting a flexible tube to a connection means is provided. The method comprises the steps of:
  providing the connection means protruding into an end of the flexible tube;
  providing a connection clamping device around the flexible tube and the connection means (5) when the connection means protrudes into the tube (1), said connection clamping device comprises two halves which are connected and locked to each other during this step;
  squeezing the flexible tube against the connection means by a rib provided on a part of the inner surface of the connection clamping device around the circumference.

The invention claimed is:
1. A connection clamping device arranged for connecting a flexible tube to a barbed end of a connection means, whereby the barbed end comprises a barb and the connection means during connection is arranged to protrude into an end of the flexible tube, characterized in that said connection clamping device comprises two halves which, during connection when the connection means protrudes into an end of the flexible tube, are arranged to be connected and locked to each other by a locking mechanism around the connection means and the flexible tube, such that the flexible tube is compressed against the connection means by a first rib provided on the inner circumference of the connection clamping device,
- wherein an inner diameter of the connection clamping device except from where the first rib is provided is larger than an outer diameter of the flexible tube and an inner diameter of the tube formed part at the position for the first rib is less than the outer diameter of the flexible tube,
- wherein the first rib is configured to create a space between the connection clamping device inner diameter and the outside diameter of the flexible tube,
- wherein a second rib is provided in the two halves, whereby the second rib is arranged to compress the flexible tube against a coned surface of the barbed end, above the barb when the connection clamping device is provided for clamping the tube to the connection means, and
- wherein a positioning rib is provided in the connection clamping device, whereby the positioning rib is arranged to be adjacent to a connection means rib on the connection means when the connection clamping device is provided for clamping the tube to the connection means for aligning the connection clamping device axially with the connection means.

2. The connection clamping device according to claim 1, wherein said connection clamping device comprises:
- a first half and a second half which when connected to each other forms a tube formed part,
- a locking mechanism arranged such that when the two halves are brought together they are locked to each other,
- a first part of the first rib provided in the first half and a second part of the first rib provided in the second half, which rib parts together form the first rib over the inner circumference of the tube formed part when the two halves are locked together,
- whereby the two halves of the connection clamping device are arranged to be positioned around and locked around the flexible tube and the connection means when the connection means protrudes into the tube and the first rib is arranged to squeeze the flexible tube against the connection means below the barb provided on the connection means.

3. The connection clamping device according to claim 1, wherein the two halves are connected to each other on one side by a living hinge.

4. The connection clamping device according to claim 1, wherein the locking mechanism is arranged on a first connection surface of each of the two halves and the locking mechanism is one or more protruding latches on one of the halves and recesses on the other of the two halves.

5. The connection clamping device according to claim 1, wherein the locking mechanism is arranged on both a first and a second connection surface of each of the two halves and the locking mechanism is one or more protruding latches on one of the halves and recesses on the other of the two halves.

6. The connection clamping device according to claim 1, wherein an indicator window is provided in a side wall of one or both of the two halves, whereby when the connection clamping device is mounted over the flexible tube and connection means the end of the flexible tube should be seen through the indicator window if the tube has been correctly connected to the connection means.

7. A method for connecting a flexible tube to a barbed end of a connection means, said method comprising the steps of:
- providing the connection means protruding into an end of the flexible tube;
- providing a connection clamping device around the flexible tube and the connection means when the connection means protrudes into the tube, said connection clamping device comprises two halves comprising a first rib, a second rib, and a positioning rib, wherein the two halves are connected and locked to each other during this step; and
- squeezing the flexible tube against the connection means by a first rib provided on a part of an inner surface of the connection clamping device around a circumference of the flexible tube, wherein the first rib is configured to create a space between part of the inner surface of the connection clamping device and the outside diameter of the flexible tube, and the second rib is configured to squeeze above the barb on the barbed end, and whereby the positioning rib is arranged to be adjacent to a connection means rib on the connection means when the connection clamping device is provided for clamping the tube to the connection means for aligning the connection clamping device axially with the connection means.

* * * * *